United States Patent [19]

Pastor et al.

[11] Patent Number: 4,730,083

[45] Date of Patent: Mar. 8, 1988

[54] PROCESS FOR THE PREPARATION OF 3,5-DIALKYL-4-HYDROXY BENZOIC ACID

[75] Inventors: Stephen D. Pastor, Yonkers; John D. Spivack, Spring Valley, both of N.Y.; Paul Odorisio, Palisades Park, N.J.

[73] Assignee: Ciba-Geigy Corporation, Ardsley, N.Y.

[21] Appl. No.: 898,794

[22] Filed: Aug. 18, 1986

Related U.S. Application Data

[63] Continuation of Ser. No. 685,369, Dec. 24, 1984, abandoned.

[51] Int. Cl.$^4$ .............................................. C07C 51/15
[52] U.S. Cl. ..................................... 562/423; 562/424
[58] Field of Search ................................ 562/423, 424

[56] References Cited

U.S. PATENT DOCUMENTS

| 3,305,484 | 2/1967 | Orloff | 562/424 X |
| 4,032,555 | 6/1977 | Bottaccio et al. | 562/423 X |
| 4,034,006 | 7/1977 | Lind et al. | 562/424 |

FOREIGN PATENT DOCUMENTS 738359 10/1955 United Kingdom .

OTHER PUBLICATIONS

Sakakibara et al., Bull. Chem. Soc. Jpn., vol. 53, 1980, pp. 279–280.

*Primary Examiner*—Howard T. Mars
*Assistant Examiner*—Patricia M. Scott
*Attorney, Agent, or Firm*—Harry Falber

[57] ABSTRACT

An improved process for the preparation of 3,5-dialkyl-4-hydroxybenzoic acid comprising the reaction of 2,6-dialkylphenol and carbon dioxide in the presence of a mono- or polyalkylene glycol ether.

5 Claims, No Drawings

PROCESS FOR THE PREPARATION OF 3,5-DIALKYL-4-HYDROXY BENZOIC ACID

This is a continuation of application Ser. No. 685,369, filed Dec. 24, 1984, now abandoned.

3,5-dialkyl-4-hydroxybenzoic acid and the various esters thereof are well known, commercially successful stabilizers of polymers subject to oxidative deterioration.

U.S. Pat. No. 3,330,859 and U.S. Pat. No. 3,681,431 are representative of the patents disclosing such compounds. The preparative processes disclosed in the patents include esterification procedures from suitable alcohols and acids, acid halides or acid anhydrides.

Other preparative approaches have also been disclosed. For example, the carboxylation of alkali metal salts of phenols with carbon dioxide is well known for the preparation of p-hydroxybenzoic acids [for a review of the Kolbe-Schmitt reaction see A. S. Linsey and H. Jeskey, Chem. Rev., 57, 583 (1957)]. The use of dipolar aprotic solvents for the carboxylation of alkali metal salts of 2,6-dialkyl phenols has also been described [see, for example, Meek, U.S. Pat. No. 3,825,593; Lind et al, U.S. Pat. No. 4,034,006 and Grosso, U.S. Pat. No. 4,072,707]. N,N-Dimethylformamide has been the preferred dipolar aprotic solvent for these processes even though it has the disadvantages of having a high boiling point (b.p. 153° C.) and known human toxicity (see, for example, M. Windholz, The Merck Index, Ninth Edition, p. 3236).

Other solvents have been explored for use in the carboxylation of phenoxides but considerably reduced yields have resulted. For example, T. Sakakihara and K. Haraquchi (Bull. Chem. Soc. Jpn. 53, 279, 1980) have shown that the carboxylation of sodium phenoxide in polyethylene glycol dimethyl ethers gives exceedingly poor yields of the hydroxybenzoic acids. In fact, there was no benzoic acid formed when sodium phenoxide was treated with carbon dioxide in 1,2-dimethoxyethane.

As a further aspect of the primary reaction approach, Grosso (U.S. Pat. No. 4,072,707) has described the use of 1 to 5 equivalents of alkali metal hydrides relative to the 2,6-dialkyl phenols as a preferred preparation of the corresponding alkali metal salts of 2,6-dialkyl phenols, notwithstanding the high cost of alkali metal hydrides relative to alkali metal hydroxides. The alkali metal salts are treated with carbon dioxide in dipolar aprotic solvents to prepare 3,5-dialkyl-4-hydroxy-benzoic acids.

The search for improved processes continues in an attempt to obtain increased yields and purity while reducing extreme reaction conditions, eliminating toxicity problems and improving reaction economics.

Accordingly, it is the primary object of this invention to provide an improved process for the preparation of 3,5-dialkyl-4-hydroxybenzoic acid.

Various other objects and advantages of this invention will become apparent from the following detailed discussion thereof.

The present invention describes a new and improved process for the preparation of 3,5-dialkyl-4-hydroxybenzoic acids from an alkali metal salt of 2,6-dialkyl phenol and carbon dioxide in the presence of a mono- or polyalkylene glycol ether solvent. The following advantages are particularly relevant to this invention:

(1) The process prescribes the use of carbon dioxide at atmospheric pressure, thereby avoiding the difficulties associated with high pressure processes.
(2) The process requires only moderate temperatures, thereby avoiding the problems and cost associated with higher temperature processes.
(3) The process is conducted in a homogeneous phase by the use of a solvent so as to avoid the difficulties associated with heterogeneous gas-solid processes.
(4) The process allows for the partial or complete substitution of metal hydroxides for the more costly metal hydrides.
(5) The process encompasses the use of polyethylene glycol dialkyl ethers of low boiling point which avoids the use of higher boiling dipolar aprotic solvents. In particular, the use of ethylene glycol dimethyl ether (boiling point 85° C.) over the previous use of N,N-dimethylformamide (boiling point 153° C.) allows for easier recovery of solvent.
(6) The preferred use of ethylene glycol dimethyl ether also avoids the health hazard associated with the known human toxicity of N,N-dimethylformamide.

The general reaction scheme of the instant inventions corresponds to the equation

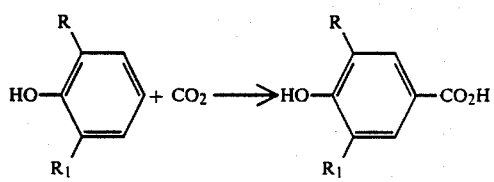

wherein R and $R_1$ independently are alkyl groups of 1 to 30 carbon atoms. Thus, branched and straight chain alkyl groups are contemplated such as methyl, ethyl, propyl, butyl, tert-butyl, octyl, decyl, dodecyl, tetradecyl, octadecyl, eicosyl and the like. Since the hindered phenols are preferred as stabilizers, branched alkyls of 4 to 8 carbon atoms, and particularly tert-butyl groups are preferred.

The reaction proceeds by reacting the 2,6-dialkyl-phenol in the presence of a strong base which functions to convert the phenol to a phenolate ion in the presence of a mono- or polyalkylene glycol ether solvent and an optional aromatic hydrocarbon solvent such as benzene, toluene, xylene, and the like. The mixture is heated to a temperature range of 30° to 60° C., whereupon the carbon dioxide is introduced below the surface of the reaction mixture for a period of generally 0.5 to 2 hours to insure complete reaction. Any excess sodium hydride is then destroyed by use of an alcohol, the reaction mixture generally adjusted to a pH of 1 to 2 with mineral acid and the 3,5-dialkyl-4-hydroxybenzoic acid recovered by conventional means.

The strong bases include alkali and alkaline earth metal and ammonium hydroxides, hydrides and amides.

The mono- and polyalkylene glycol ethers correspond to the formula

wherein $R_5$ and $R_7$ are independently lower alkyl of 1 to 8 carbon atoms,
$R_6$ is hydrogen or lower alkyl of 1 to 8 carbon atoms,
n is 0, 1 or 2, and m is 1 to 9, and preferably m is 2 to 5.

Suitable glycol ethers are ethylene glycol dimethyl ether, diethylene glycol dimethyl ether, diethylene glycol diethyl ether, triethylene glycol dibutyl ether, tripropylene glycol dimethyl ether, tetraethylene glycol dimethyl ether, tetraethylene glycol diethyl ether and pentaethylene glycol monoethyl ether. The mono- and polyethylene glycol dialkyl ethers are preferred such as the ethylene glycol dimethyl ether, diethylene glycol dimethyl ether and tetraethylene glycol dimethyl ether.

Product yields in excess of 80% are generally obtained. The resulting products are readily available for use as stabilizers either in their acid or ester form.

The following examples illustrate the embodiments of this invention.

EXAMPLE 1

A reaction vessel was charged with a suspension of 4.74 grams (0.198 mol) of sodium hydride in 150 ml of dry ethylene glycol dimethyl ether to which was added dropwise at 20°-25° C. a solution of 20.6 grams (0.10 mol) of 2,6-di-tert-butylphenol in 150 ml of ethylene glycol dimethyl ether. After the addition was complete, the reaction mixture was warmed to 50° to 60° C. for a period of 1.5 hours and then carbon dioxide was introduced through a gas-disparging tube below the surface of the reaction mixture for 20 hours. The reaction mixture was cooled to 5° C. and the excess of sodium hydride was destroyed carefully with 30 ml of methyl alcohol. After hydrogen evolution ceased, the reaction mixture was adjusted to a pH of 2 with 1N hydrochloric acid and then was diluted with 1.6 liters of water. The resultant precipitate was collected by filtration and was dried in vacuo.

The solid was triturated with 150 ml of petroleum ether at reflux to give 22.6 grams (90.4%) of an off-white solid, m.p. 205°-209° C.

EXAMPLE 2

The procedure of Example 1 was repeated using 4.74 grams (0.198 mol) of sodium hydride, 20.6 grams (0.10 mol) of 2,6-di-tert-butylphenol and 300 ml of tetraethylene glycol dimethyl ether to give 21.0 grams (84%) of an off-white solid, m.p. 205°-208° C.

EXAMPLE 3

A reaction vessel was charged with a stirred mixture of 20.6 grams (0.10 mol) of 2,6-di-tert-butylphenol, 4.0 grams (0.10 mol) of sodium hydroxide in 3.9 grams of water and 250 ml of toluene. The reaction mixture was heated at reflux under nitrogen and the water was collected in a Dean-Stark trap. After 4.7 ml of $H_2O$ was collected, the mixture was cooled and 300 ml of tetraethylene glycol dimethyl ether was added to the reaction mixture. The mixture was heated in vacuo during which time 220 ml of toluene was removed by distillation. The cooled reaction mixture was admixed with 0.24 grams (0.01 mol) of sodium hydride. The mixture was heated to 60° C. and then carbon dioxide was introduced through a gas-disparging tube below the surface of the reaction mixture for 20 hours. The reaction mixture was cooled to 5° C. and any residual sodium hydride was destroyed with 5 ml of methyl alcohol. After hydrogen evolution ceased, the reaction mixture was adjusted to a pH of 2 with 1N hydrochloric acid and then was diluted with 1 liter of water and sequentially extracted with two-100 ml portions of ether and one 100 ml portion of chloroform. The organic extracts were combined and dried over $Na_2SO_4$. The solvent was removed in vacuo and the residue was triturated with 150 ml of petroleum ether at reflux to give 17.3 grams (69%) of an off-white solid, m.p. 205°-209° C.

EXAMPLE 4

The procedure of Example 3 was repeated using 20.6 grams (0.10 mol) of 2,6-di-tert-butylphenol, 6.2 grams (0.11) of potassium hydroxide in 7.3 grams of water, 250 ml of toluene and 250 ml of tetraethylene glycol dimethyl ether. After trituration with 125 ml of petroleum ether at reflux, 10.8 grams (43%) of an off-white solid was obtained, m.p. 206°-208° C.

Summarizing, it is seen that this invention provides an improved process for preparing 3,5-dialkyl-4-hydroxybenzoic acid. Variations may be made in proportions, procedures and materials without departing from the scope of the invention as defined by the following claims.

What is claimed is:

1. A process for preparing 3,5-dialkyl-4-hydroxybenzoic acid which consists essentially of converting 2,6-dialkylphenol to the corresponding phenolate in the presence of an alkali or alkaline-earth metal hydroxide, hydride or amide and a mono- or polyalkylene glycol ether selected from the group consisting of ethylene glycol dimethyl ether and tetraethylene glycol dimethyl ether, reacting the resulting phenolate with carbon dioxide at a temperature of from about 30°-60° C. and isolating the 3,5-dialkyl-4-hydroxybenzoic acid.

2. The process of claim 1, wherein said alkyl groups independently contain from 1 to 30 carbon atoms.

3. The process of claim 2, wherein said alkyl groups independently are branched alkyl groups of 4 to 8 carbon atoms.

4. The process of claim 3, wherein said alkyl groups are tert-butyl.

5. The process of claim 1, wherein the reaction mixture is adjusted to a pH level of 1 to 2 prior to isolation of the benzoic acid.

* * * * *